(12) United States Patent
Stoddard et al.

(10) Patent No.: US 6,316,231 B1
(45) Date of Patent: Nov. 13, 2001

(54) BACTERIAL STRAINS FOR THE PRODUCTION OF 2-KETO-L-GULONIC ACID

(75) Inventors: Steven F. Stoddard, Decatur; Hungming J. Liaw; John D'Elia, both of Champaign, all of IL (US)

(73) Assignee: Archer-Daniels-Midland Company, Decatur, IL (US)

(*) Notice: Subject to any disclaimer, the term of this patent is extended or adjusted under 35 U.S.C. 154(b) by 0 days.

(21) Appl. No.: 09/393,665

(22) Filed: Sep. 10, 1999

Related U.S. Application Data

(60) Provisional application No. 60/099,860, filed on Sep. 11, 1998.

(51) Int. Cl.[7] .............................. C12P 7/60; C12N 1/20
(52) U.S. Cl. ....................................... 435/138; 435/252.1
(58) Field of Search .................................. 435/138, 243, 435/252.1

(56) References Cited

U.S. PATENT DOCUMENTS

| | | | |
|---|---|---|---|
| 3,043,749 | 7/1962 | Huang | 195/47 |
| 3,234,105 | 2/1966 | Motizuki et al. | 195/49 |
| 3,907,639 | 9/1975 | Makover et al. | 195/36 |
| 3,912,592 | 10/1975 | Makover et al. | 195/31 |
| 4,877,735 | 10/1989 | Nogami et al. | 435/138 |
| 4,892,823 | 1/1990 | Imai et al. | 435/138 |
| 4,933,289 | 6/1990 | Imai et al. | 435/253.2 |
| 4,935,359 | 6/1990 | Yin et al. | 435/138 |
| 4,945,048 | 7/1990 | Uchihori et al. | 435/105 |
| 4,960,695 | 10/1990 | Hoshino et al. | 435/42 |
| 4,994,382 | 2/1991 | Ameyama et al. | 435/119 |
| 5,082,785 | 1/1992 | Manning et al. | 435/252.32 |
| 5,312,741 | 5/1994 | Hoshino et al. | 435/42 |
| 5,344,768 | 9/1994 | Urakami | 435/119 |
| 5,437,989 | 8/1995 | Asakura et al. | 435/190 |
| 5,474,924 | 12/1995 | Nogami et al. | 435/138 |
| 5,541,108 | 7/1996 | Fujiwara et al. | 435/252.1 |
| 5,834,231 | 11/1998 | Stoddard et al. | 435/42 |

FOREIGN PATENT DOCUMENTS

| | | |
|---|---|---|
| 1081470 | 2/1994 | (CN) . |
| 0 213 591 | 3/1987 | (EP) . |
| 0 221 707 | 5/1987 | (EP) . |
| 0 276 832 A2 | 8/1988 | (EP) . |
| 0 278 447 | 8/1988 | (EP) . |
| 0 206 471 B1 | 10/1992 | (EP) . |
| 0 518 136 | 12/1992 | (EP) . |
| 0 832 974 | 4/1998 | (EP) . |
| 41-159 | 1/1966 | (JP) . |
| 41-160 | 1/1966 | (JP) . |
| 41-5907 | 3/1966 | (JP) . |
| 51-40154 | 4/1976 | (JP) . |
| 59 113896 | 6/1984 | (JP) . |
| 03 294281 | 12/1991 | (JP) . |
| 7-67673 | 3/1995 | (JP) . |
| 7-250671 | 10/1995 | (JP) . |
| 08 245702 | 9/1996 | (JP) . |
| 526660 | 10/1976 | (SU) . |
| WO 98/17819 | 4/1998 | (WO) . |
| WO 98 33885 | 8/1998 | (WO) . |

OTHER PUBLICATIONS

Pelczar et al. Microbiology. 1972. McGraw–Hill, Inc. pp 140, 930, and first page of chapter 3.*

Ameyama, M., et al., "Existence of a Novel Prosthetic Group, PQQ, in Membrane–Bound, Electron Transport Chain–Linked, Primary Dehydrogenases of Oxidative Bacteria," *FEBS Lett.* 130:179–183 (1981).

Bishop, A., et al., "Pyrroloquinoline Quinone: A Novel Vitamin?," *Nutrition Rev.* 56:287–293 (Oct. 1998).

Dekker, R.H., et al., "Covalent Addition of $H_2O$, Enzyme Substrates and Activators to Pyrrolo–quinoline Quinone, the Coenzyme of Quinoproteins," *Eur. J. Biochem.* 125:69–73 (1982).

Follettie, M.T., "DNA Technology for *Corynebacterium glutamicum*: Isolation and Characterization of Amino Acid Biosynthetic Genes," Ph.D. Thesis, Massachusetts Institute of Technology (1989).

Galanos, C., et al., "A New Method for the Extraction of R Lipopolysaccharides," *Eur. J. Biochem.* 9:245–249 (1969).

*Biotechnology—A Comprehensive Treatise in 8 Volumes*, Kieslich, K., ed., Verlag Chemie, Weinheim, Germany, vol. 6a, pp. 436–437 (1984).

Martin, C.K.A., and Perlman, D., "Conversion of L–Sorbose to 2–Keto–L–gulonic Acid by Mixtures of Immobilized Cells of *Gluconobacter melanogenus* IFO 3293 and *Pseudomonas* Species," *Eur. J. Appl. Microbiol.* 3:91–95 (1976).

Morrison, D.A., "Transformation in *Escherichia coli*: Cryogenic Preservation of Competent Cells," *J. Bacteriol.* 132:349–351 (1977).

Qureshi, N., et al., "Position of Ester Groups in the Lipid A Backbone of Lipopolysaccharides Obtained from *Salmonella typhimurium*," *J. Biol. Chem.* 258:12947–12951 (1983).

Qureshi, N., et al., "Location of Fatty Acids in Lipid A Obtained from Lipopolysaccharide of *Rhodopseudomonas sphaeroides* ATCC 17023," *J. Biol. Chem.* 263:5502–5504 (1988).

(List continued on next page.)

Primary Examiner—James Ketter
Assistant Examiner—Lisa Gansheroff
(74) Attorney, Agent, or Firm—Sterne, Kessler, Goldstein & Fox

(57) ABSTRACT

The present invention relates to novel bacterial strains useful for the production of 2-keto-L-gulonic acid. The present invention further relates to the use of these strains for the production of 2-keto-L-gulonic acid by fermentative conversion of L-sorbose. The present invention further relates to the use of these novel bacterial strains for the production of pyrroloquinoline quinone and a nontoxic lipopolysaccharide. Also described is the strains of the present invention transformed by a vector.

20 Claims, 1 Drawing Sheet

OTHER PUBLICATIONS

Qureshi, N., et al., "Complete Structural Determination of Lipopolysaccharide Obtained from Deep Rough Mutant of *Escherichia coli,*" *J. Biol. Chem.* 263:11971–11976 (1988).

Strittmatter, W., et al., "Nontoxic Lipopolysaccharide from *Rhodopseudomonas sphaeroides* ATCC 17023," *J. Bacteriol.* 155:153–158 (1983).

Tsukada, Y., and Perlman D., "The Fermentation of L–Sorbose by *Gluconobacter melanogenus*: General Characteristics of the Fermentation," *Biotechnology and Bioengineering XIV*:799–810 (1972).

"The Genetic Improvement of Product Formation," in *Molecular Biology and Biotechnology*, Walker, J.M., and Gingold, E.B., eds., Royal Society of Chemistry, London, Great Britain, pp. 15–20 (1988).

Yin, G.–l., et al., "Studies on the Production of Vitamin C Precursor 2–Keto–L–Gulonic Acid from L–Sorbose by Fermentation. I. Isolation, Screening and Identification of 2–Keto–L–Gulonic Acid Producing Bacteria," *Acta Microbiol. Sinica* 20:246–251 (1980).

Yin, G.–l., et al., "Studies on the Production of Vitamin C Precursor 2–Keto–L–Gulonic Acid from L–Sorbose by Fermentation," *Acta Microbiol. Sinica* 21:185–191 (1981).

Zuckerman, S.H., and Qureshi, N., "In Vivo Inhibition of Lipopolysaccharide–Induced Lethality and Tumor Necrosis Factor Synthesis by *Rhodobacter sphaeroides* Diphosphoryl Lipid A Is Dependent on Corticosterone Induction," *Infection and Immunity* 60:2581–2587 (1992).

English Translation of Yin, G.–l., et al., "Studies on the Production of Vitamin C Precursor 2–Keto–L–Gulonic Acid from L–Sorbose by Fermentation. I. Isolation, Screening and Identification of 2–Keto–L–Gulonic Acid Producing Bacteria," *Acta Microbiol. Sinica* 20:246–251 (1980).

English Translation of Yin, G.–l., et al., "Studies on the Production of Vitamin C Precursor 2–Keto–L–Gulonic Acid from L–Sorbose by Fermentation," *Acta Microbiol. Sinica* 21:185–191 (1981).

English Translation of JP 41–159.

English Translation of JP 41–160.

English Translation of JP 41–5907.

Abstract of SU 526660, Derwent World Patents Index, WPI Account No.: 77–48308Y/27.

Abstract of CN 1081470, Derwent World Patents Index, WPI Account No.: 95–155907/21.

Abstract of JP 7–250671, Japio No. 04958071.

English Language abstract of JP 59 113896 (Document AN3), Derwent World Patent Index, WPI Accession No. 1984–198567.

English Language abstract of JP 03 294281 (Document AO3), Derwent World Patent Index, WPI Accession No. 1992–052015.

English Language abstract of JP 08 245702 (Document AP3), Derwent World Patent Index, WPI Accession No. 96–482261.

* cited by examiner

BACTERIAL STRAINS FOR THE PRODUCTION OF 2-KETO-L-GULONIC ACID

CROSS REFERENCE TO RELATED APPLICATIONS

This application hereby claims priority benefit to U.S. application Ser. No. 60/099,860 filed Sep. 11, 1998, which is herein incorporated by reference.

BACKGROUND OF THE INVENTION

1. Field of the Invention

The present invention relates to novel bacterial strains useful for the production of 2-keto-L-gulonic acid. The present invention further relates to the use of these strains for the production of 2-keto-L-gulonic acid by fermentative conversion of L-sorbose. The present invention further relates to the use of these novel bacterial strains for the production of pyrroloquinoline quinone and a nontoxic lipopolysaccharide. Also described are the strains of the present invention transformed by a vector.

2. Background Information

2-Keto-L-gulonic acid ("2-KLG") is a significant intermediate in the preparation of L-ascorbic acid (vitamin C), an essential nutrient. 2-KLG has been synthesized in the past on an industrial scale using the Reichstein method (*Helvetica Chimica Acta* 7:311 (1934)). This method, however, has a number of disadvantages for commercial application, including the use of large quantities of solvents and the involvement of a number of complex reaction steps.

Accordingly, as an alternative to the Reichstein method, a number of processes employing one or more microorganisms have been developed to produce 2-KLG by fermentation. U.S. Pat. No. 2,421,611, for example, discloses a method involving microbial oxidation of D-glucose to 5-keto-D-gluconic acid, followed by chemical or microbial reduction to L-idonic acid and subsequent microbial oxidation to 2-KLG. Japanese Patent Publication Nos. 39-14493, 53-25033, 56-15877 and 59-35290, for example, disclose similar processes involving the microbial oxidation of D-glucose to 2,5-diketo-D-gluconic acid followed by microbial or chemical reduction to 2-KLG.

These methods, however, also suffer from a number of disadvantages that reduce their usefulness in commercial production of 2-KLG. For example, the chemical reduction steps in these methods (ie. the reduction of 5-keto-D-gluconic acid to L-idonic acid and 2,5-diketo-D-gluconic acid to 2-KLG) are accompanied by problems with controlling the stereochemistry of reduction (thus producing D-gluconic acid and 2-keto-D-gluconic acid, respectively, as byproducts) which, in turn, reduces the yield of 2-KLG. Alternatively, when this reduction is performed by one or more microorganisms, excess sugar is required to provide an energy source for the reduction, which also reduces the yield of 2-KLG.

In view of these problems, an alternate pathway has been employed for the fermentative production of 2-KLG, which involves only oxidation of L-sorbose to 2-KLG via a sorbosone intermediate. A number of processes have been developed using this pathway that employ a wide range of microorganisms from the genera Gluconobacter, such as *Gluconobacter oxydans* (U.S. Pat. Nos. 4,935,359; 4,960,695; 5,312,741; and 5,541,108), Pseudogluconobacter, such as *Pseudogluconobacter saccharoketogenes* (U.S. Pat. No. 4,877,735; European Patent No. 221 707), Pseudomonas, such as *Pseudomonas sorbosoxidans* (U.S. Pat. Nos. 4,933,289 and 4,892,823), and mixtures of microorganisms from these and other genera, such as Acetobacter, Bacillus, Serratia, Mycobacterium, and Streptomyces (U.S. Pat. Nos. 3,912,592; 3,907,639; and 3,234,105).

These processes, however, suffer from certain disadvantages that limit their usefulness for commercial production of 2-KLG. For example, the processes referenced above that employ *G. oxydans* also require the presence of an additional "helper" microbial strain, such as *Bacillus megaterium*, or commercially unattractive quantities of yeast or growth components derived from yeast in order to produce sufficiently high levels of 2-KLG for commercial use. Similarly, the processes that employ Pseudogluconobacter can require medium supplemented with expensive and unusual rare earth salts or the presence of a helper strain, such as *B. megaterium*, and/or the presence of yeast in order to achieve commercially suitable 2-KLG concentrations and efficient use of sorbose substrate. Other processes that employ *Pseudomonas sorbosoxidans* also include commercially unattractive quantities of yeast or yeast extract in the medium.

Pyrroloquinoline quinone (PQQ) (2,7,9-tricarboxy-1H-pyrrolo[2,3-f]quino-line-4,5-dione) was initially isolated from cultures of methylotrophic (methanol-utilizing) bacteria and later was found to be present in many animal tissues. The structure of PQQ follows:

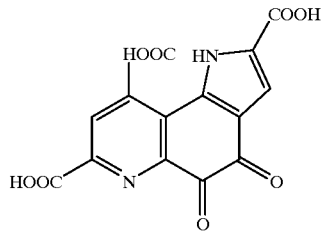

PQQ may be a novel vitamin as it is believed to be essential for normal growth and development. When fed to animals as a supplement, PQQ prevents oxidative changes that would ordinarily occur. Furthermore, PQQ increases nerve growth factor synthesis in mouse astrogial cells and has potential for a therapeutic role in the brain. (Bishop et al., "Pyrroloquinoline Quinone: A Novel Vitamin," *Nutrition Reviews* 56:287–293 (1998).

Organic chemical synthesis is the conventional means to produce PQQ. However, organic chemical synthesis has numerous disadvantages. For example, chemical synthesis is uneconomical and time consuming because the synthesis requires multiple and sometimes complicated reaction steps and produces low yields.

Accordingly, the need to overcome the disadvantages of chemical synthetic techniques for production of PQQ has been partially met by bacterial strains useful for the production of PQQ. (U.S. Pat. Nos. 4,994,382 and 5,344,768). However, there still remains a need for more efficient and economical PQQ-producing microorganism strains.

Lipopolysaccharide (LPS) is an amphipathic molecule which is a cell wall component of many gram-negative bacteria. It has been implicated in much of the pathophysiology associated with gram negative infections in humans and animals. LPS from *Rhodobacter sphaeroides* is nontoxic and has several uses as a immuno-modulator and antitumor agent. However, there are several disadvantages associated with producing nontoxic LPS through *Rhodo-*

*bacter sphaeroides*, for example, the inconvenience of culturing phototrophically.

SUMMARY OF THE INVENTION

The present invention provides microorganism strains which efficiently produce 2-keto-L-gulonic acid.

Another embodiment of the present invention is directed to strains for production of 2-keto-L-gulonic acid in cooperation with helper strains.

A further embodiment of the present invention provides a method for producing PQQ.

Another embodiment of the present invention is to provide a method for producing a nontoxic LPS.

An additional embodiment of the present invention is to provide the bacterial strains of the present invention transformed by a vector, and a method for the transformation of the bacterial strains by a vector.

These and other embodiments are accomplished by the methods of the present invention, which, in a first embodiment, is directed to a culture of any of the microorganism strains ADM 291-19 (NRRL B-30035), ADM 62A-12A (NRRL B-30037N), ADM 266-13B (NRRL B-30036), or mutants thereof.

Other features and advantages of the present invention will be set forth in the detailed description of preferred embodiments that follows, and in part will be apparent from the description or may be learned by practice of the invention. These advantages of the invention will be realized and attained by the methods particularly pointed out in the written description and claims hereof.

It is to be understood that both the foregoing general description and the following detailed description are exemplary and explanatory only and are intended to provide further explanation of the invention as claimed.

DETAILED DESCRIPTION OF THE INVENTION

Figure 1:
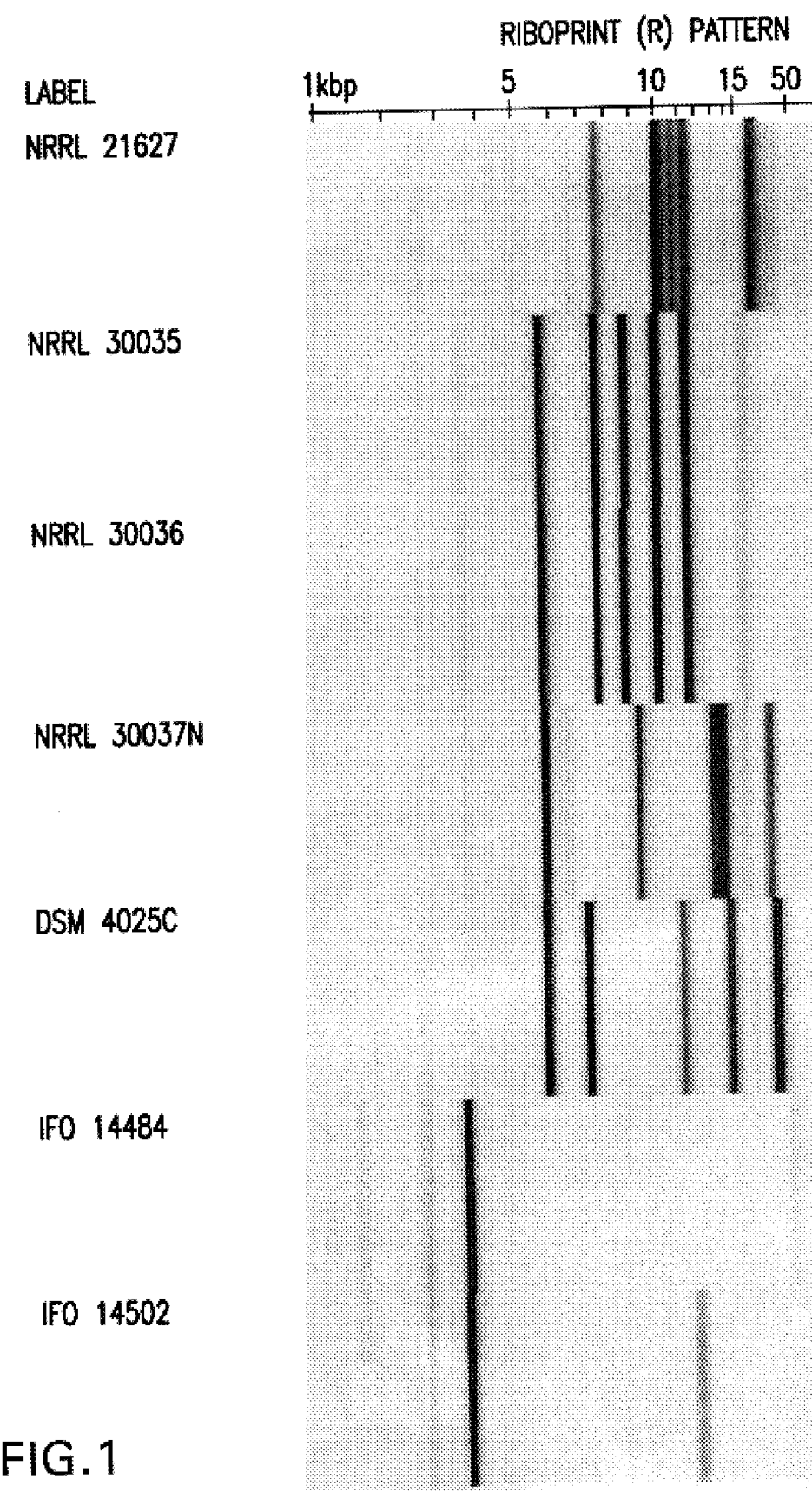
FIG. 1 is a depiction of the RiboPrint® patterns of bacterial strains capable of producing 2-KLG from L-sorbose. RiboPrint® patterns were obtained from the following bacterial strains: ADM X6L (NRRL B-21627), ADM 291-19 (NRRL B-30035), ADM 266-13B (NRRL B-30036), ADM 62A-12A(NRRL B-30037N), DSM 4025C (a reisolate of the small-colony component strain of the mixed culture deposit DSM 4027, U.S. Pat. No. 4,935,359), *Pseudogluconobacter saccharoketogenes* strain IFO 14484 and *Pseudomonas sorbosoxidans* strain IFO 14502.

In a first embodiment, the present invention is directed to a biologically pure culture of a microorganism strain having the identifying characteristics of a strain selected from the group consisting of ADM 291-19 (NRRL B-30035), ADM 62A-12A (NRRL B-30037N), ADM 266-13B (NRRL B-30036), or mutants thereof. The microorganism strains of the present embodiment are capable of producing 2-KLG from L-sorbose by fermentation in pure culture, i.e., in the absence of one or more additional microorganism strain(s).

In a further embodiment, microorganism strains of the present invention and of strain ADM X6L (NRRL B-21627, U.S. Pat. No. 5,834,231) are capable of producing PQQ from a suitable carbon source.

Strains ADM 291-19 and ADM 266-13B were deposited at the Agricultural Research Service Culture Collection (NRRL), 1815 North University Street, Peoria, Ill. 61604, USA, on Jun. 18, 1998, under the provisions of the Budapest Treaty and assigned accession numbers NRRL B-30035 and NRRL B-30036, respectively. Strain ADM 62A-12A was deposited at the NRRL on Aug. 25, 1998 and assigned assession number NRRL B-30037N. The characteristics of strains NRRL B-30035, NRRL B-30037N, and NRRL B-30036 include, but are not limited to:

(1) Cell Morphology—gram-negative; may be gram variable in older cultures; tiny rods or coccobacilli; cells appear singly and in pairs; may be pleiomorphic; may form short chains or long irregular cells; do not form spores;

(2) Colony Morphology—punctiform, convex, entire, smooth, butyrous and translucent; beige or brown coloration in older colonies on some media;

(3) Pigment—colonies produce brown diffusable pigment, especially on nutrient-rich media containing calcium carbonate and with fructose as the carbon source.

(4) Physiological characteristics:
 (a) catalase: positive;
 (b) oxidase: positive
 (c) gelatinase: negative;

(5) Cultural Characteristics:
 (a) Brain Heart Infusion agar: growth;
 (b) growth occurs on DM liquid basal medium (Table 5), without NaCl, or in agar-solidified DM basal medium;
 (c) does not form pellicle or ring within 24 hours in standing glucose or mannitol broth culture at pH in range of 4.0–5.0;
 (d) growth in DM liquid basal medium (Table 5), without NaCl, or in agar-solidified DM basal medium, occurs at 4° C. but not at 37° C. Optimum growth temperature is between 25° C.–30° C. in DM liquid basal medium (Table 5), without NaCl, or in agar-solidified DM basal medium;
 (e) optimum pH for growth in DM basal medium (Table 5), without NaCl, or in agar-solidified basal medium, is between pH 7.0 and pH 8.0;

(6) Antibiotic resistance-sensitive to amikacin, augmentin (amoxicillin plus clavulonic acid), ampicillin, cefazolin, cefoxitin, ceftazidime, ceftiofur, cephalothin, enrofloxacin, florfenicol, gentamicin, imipenem, kanamycin, sarafloxicin, tetracycline, ticarcillin, and tilmicosin, but resistant to tribrissen (augmentin plus sulfamethozole), as determined by minimum inhibitory concentration (MIC), based on physiologically attainable concentrations of antibiotic, employing the commercial "Pasco" system; and (7) RiboPrint® Analysis:
 RiboPrint® is an automated ribotyping system that generates and analyzes genetic fingerprints of bacteria. The genetic fingerprinting patterns are normalized digital representations of the genetic data for each sample. The patterns obtained by this method are useful for differentiating not only between organisms of different species, but also between different strains of the same species. RiboPrint® patterns obtained for strains NRRL B-30035 (ADM 291-19), NRRL B-30037N (ADM 62A-12A), and NRRL B-30036 (ADM 266-13B) and a number of comparative strains known to be capable of producing 2-KLG from L-sorbose are depicted in FIG. 1.

The uniqueness of bacterial strains can be demonstrated from their RiboPrint® patterns in cases where these patterns are different. In cases where two strains give RiboPrint® patterns that are non-distinguishable, the RiboPrint® data are inconclusive and other methods are required to show the uniqueness of strains. One such method is DNA reassociation, in which the strains' degree of relatedness over the entire bacterial chromosome is estimated. This can be done by quantitative, reciprocal cross-hybridization of chromosomal DNA from the two strains. In the case of strains NRRL B-30035 (ADM 291-19) and NRRL B-30036 (ADM 266-13B), results from such studies showed a chromosomal similarity of less than 70%, a result that, in modern bacterial taxonomy, is often associated with strains belonging to separate species (Wayne, L. G. et al., *Int. J System. Bacteriol.* 37:463–464 (1987)). Thus, the DNA reassociation data show unequivocally that strains NRRL B-30035 (ADM 291-19) and NRRL B-30036 (ADM 266-13B) are unique and different from one another.

Bacterial strain ADM X6L (NRRL B-21627) and mutants thereof producing 2-KLG from L-sorbose via fermentation are disclosed in U.S. Pat. No. 5,834,231, issued Nov. 10, 1998 and U.S. application Ser. No. 08/893,598, filed Jul. 11, 1997, respectively. The strain and its mutants disclosed in this application are distinct from those in the present invention, as can be seen from a comparison of their RiboPrint® patterns shown in FIG. 1.

In addition to biologically pure strains NRRL B-30035 (ADM 291-19), NRRL B-30037N (ADM 62A-12A), and NRRL B-30036 (ADM 266-13B) mutants thereof may also be employed for the production of 2-KLG, provided that these mutants are also capable of producing 2-KLG from L-sorbose.

Microorganism strains of the present invention, and mutants thereof, and strain NRRL B-21627 (ADM X6L), and mutants thereof, may also be employed for production of PQQ, provided the mutants are also capable of producing PQQ.

As used herein, a "biologically pure" strain is intended to mean the strain separated from materials with which it is normally associated in nature. Note that a strain associated with other strains, or with compounds or materials that it is not normally found with in nature, is still defined as "biologically pure." A monoculture of a particular strain is, of course, "biologically pure."

As used herein, a mutant of a given strain of the present invention is derived from one of the strains of the present invention, namely, NRRL B-30035 (ADM 291-19), NRRL B-30037N (ADM 62A-12A), or NRRL B-30036 (ADM 266-13B) or microorganism strain NRRL B-21627 (ADM X6L).

Illustrative examples of suitable methods for preparing mutants of the inventive microorganism strains include, but are not limited to: mutagenesis by irradiation with ultraviolet light or X-rays, or by treatment with a chemical mutagen such as nitrosoguanidine (N-methyl-N'-nitro-N-nitrosoguanidine), methylmethanesulfonate, nitrogen mustard and the like; gene integration techniques, such as those mediated by insertional elements or transposons or by homologous recombination of transforming linear or circular DNA molecules; and transduction mediated by bacteriophages. These methods are well known in the art and are described, for example, in J. H. Miller, *Experiments in Molecular Genetics,* Cold Spring Harbor Laboratory Press, Cold Spring Harbor, N.Y. (1972); J. H. Miller, *A Short Course in Bacterial Genetics,* Cold Spring Harbor Laboratory Press, Cold Spring Harbor, N.Y. (1992); M. Singer and P. Berg, *Genes & Genomes,* University Science Books, Mill Valley, Calif. (1991); J. Sambrook, E. F. Fritsch and T. Maniatis, *Molecular Cloning: A Laboratory Manual,* 2d ed., Cold Spring Harbor Laboratory Press, Cold Spring Harbor, N.Y. (1989); P. B. Kaufman et al., *Handbook of Molecular and Cellular Methods in Biology and Medicine,* CRC Press, Boca Raton, Fla. (1995); *Methods in Plant Molecular Biology and Biotechnology,* B. R. Glick and J. E. Thompson, eds., CRC Press, Boca Raton, Fla. (1993); and P. F. Smith-Keary, *Molecular Genetics of Escherichia coli,* The Guilford Press, New York, NY (1989).

A 2-KLG producing mutant may or may not have the same identifying biological characteristics of the parent or progenitor strain, as long as the mutant produces 2-KLG.

A PQQ producing mutant similarly may or may not have the same identifying biological characteristics of the parent or progenitor strain, as long as the mutant produces PQQ.

Mutated strains derived from the inventive organisms NRRL B-30035 (ADM 291-19), NRRL B-30037N (ADM 62A-12A), or NRRL B-30036 (ADM 266-13B), or mutants derived from NRRL B-21627 (ADM X6L) using known methods are then preferably selected or screened for improved 2-KLG and/or PQQ production potential or for other desirable properties related to their utility in producing 2-KLG from L-sorbose, and/or their utility in producing PQQ.

In accordance with the present invention, an inventive microorganism strain or a mutant thereof is contacted with L-sorbose for a sufficient time and then the accumulated 2-KLG is isolated. Preferably, the microorganism strain is cultivated in a natural or synthetic medium containing L-sorbose for a period of time for 2-KLG to be produced and the accumulated 2-KLG is subsequently isolated. Alternatively, a preparation derived from the cells of the microorganism strain may be contacted with L-sorbose for a sufficient time and the accumulated 2-KLG may then be isolated.

In agreement with the present invention, an inventive microorganism strain or a mutant thereof is cultured in a culture medium that comprises a carbon source and a nitrogen source. The carbon source can be various sugar alcohols, polyols, aldol sugars or keto sugars including but not limited to arabinose, cellobiose, fructose, glucose, glycerol, inositol, lactose, maltose, mannitol, mannose, rhamnose, raffinose, sorbitol, sorbose, sucrose, trehalose, pyruvate, succinate or methylamine or other substrates which may be determined by one skilled in the art. The medium preferably contains a polyol or aldol sugar, and even more preferably mannitol, inositol, sorbose, glycerol, sorbitol, lactose and arabinose as the carbon source at a concentration of 0.1% to 20.0% by weight. All of the carbon source may be added to the medium before the start of culturing, or it may be added step by step or continuously during culturing.

As used herein, "a preparation derived from the cells" is intended to mean any and all extracts of cells from the culture broths of an inventive strain or a mutant thereof, acetone dried cells, immobilized cells on or within supports, such as polyacrylamide gel, K-carrageenan, calcium alginate and the like, and similar preparations.

An illustrative example of such a procedure involves adding L-sorbose and $CaCO_3$ in a suitable aqueous buffer, such as 2-(N-methylmorpholino) ethanesulfonic acid (pH 6.5; 0.5 M), to an aqueous extract of the microorganism strain in a shaker flask. This reaction preferably proceeds at a pH in the range of 6.0 to 8.0 at a temperature in the range of 20° C. to 40° C. for about 1 to 100 hours. The concentration of L-sorbose should be about 0.1 to 10% w/v, more preferably about 0.3 to 6% (w/v) and the amount of the preparation derived from the cells of strain NRRL B-30035 (ADM 291-19), NRRL B-30037N (ADM 62A-12A) or NRRL B-30036 (ADM 266-13B) or a mutant thereof should be about 1 to 30 mg/ml. After shaking for a sufficient period of time under temperature and pH conditions empirically determined to maximize 2-KLG yield, the accumulated 2-KLG may be isolated by conventional methods.

The medium used herein may be solid or liquid, synthetic (i.e. man-made) or natural, and contains sufficient nutrients for the cultivation of the inventive microorganism strains. Preferably, the medium employed is a liquid medium, more preferably a synthetic liquid medium.

In the various embodiments of the method (which as used herein, is synonymous with process) of the present invention, the starting material, L-sorbose, may be present in the medium prior to introduction of an inventive microorganism strain or may be added to the medium after introduction of the strain, either all at once at the beginning or continuously or in installments over the course of cultivation, or may be generated in situ by fermentative conversion of D-sorbitol. The amount of L-sorbose employed may be determined empirically by one skilled in the art, but is at least sufficient for the microorganism strain to produce at least about 40 g/L of 2-KLG. Preferably, L-sorbose comprises from 3 to 30% (w/v) of the culture medium, more preferably from 5 to 20%.

In a preferred embodiment of the present invention, the L-sorbose starting material is generated in situ by fermentative conversion of D-sorbitol using a suitable microorganism or mixture of microorganisms. Any microorganism or mixture of microorganisms that can convert D-sorbitol to L-sorbose in the presence of NRRL B-30035 (ADM 291-19), NRRL B-30037N (ADM 62A-12A) or NRRL B-30036 (ADM 266-13B) or a mutant thereof while not adversely affecting its ability to convert L-sorbose to 2-KLG may be employed. Preferably, the microorganism employed is a strain of *Gluconobacter oxydans*, more preferably *G. oxydans* strain ATCC 621 or *G. oxydans* strain IFO 3293. According to this preferred embodiment of the present invention, the D-sorbitol starting material may be present in the medium prior to introduction of one or more of the microorganisms or may be added to the medium after introduction of one or more of the microorganisms, either all at once at the beginning or continuously or in installments over the course of cultivation.

The natural or synthetic culture media used in the above and below described embodiments of the invention also contain anitrogen source, suitable inorganic salts, and, as appropriate, various trace nutrients, growth factors and the like suitable for cultivation of the microorganism strain, and may also contain at least one supplementary carbon source. The amount of each of these additional ingredients to be employed is preferably selected to maximize 2-KLG and/or PQQ and/or LPS production. Such amounts may be determined empirically by one skilled in the art according to the various methods and techniques known in the art.

In a particularly preferred embodiment of the present invention, the culture medium used for 2-KLG production contains about 10% (w/v) of L-sorbose, about 3% (wt. dry solids/v) of corn steep liquor, and about 0.2% (w/v) of $MgSO_4.7H_2O$, with pH controlled using $NH_4OH$, $Ca(OH)_2$ or $CaCO_3$.

In a particularly preferred embodiment of the present invention, the culture medium used for PQQ production contains about 5 to 40 g/L of mannitol, glucose, sorbose or inositol, preferably 10 to 20 g/L of mannitol, glucose, sorbose or inositol and the culturing is carried out at a temperature of between 0° C. to 40° C., preferably 2° C. to 35° C., and even more preferably 20° C. to 35° C. The pH of the medium is generally 6 to 9, preferably 6.5 to 8.0. The culturing time is generally 20 to 150 hours, preferably 20 to 50 hours. In the present embodiment, PQQ is accumulated in the cells and/or culture medium. An illustrative example of media for PQQ production from ADM X6L (NRRL B-21627) is DM Basal Medium (Table 5), pH 6.0–7.8. In the case of ADM 62A-12A, 266-13B, and 291-19 strains, DM Basal Medium without NaCl is used. In place of mannitol, any other polyols or sugar alcohols such as myo-inositol, sorbose and glucose can be used.

Medium for use in preparing inoculum may contain additional components as appropriate, such as peptone, N-Z Amine, enzymatic soy hydrosylate, additional yeast extract, malt extract, supplemental carbon sources and various vitamins.

Illustrative examples of suitable supplemental carbon sources include, but are not limited to: other carbohydrates, such as glucose, fructose, mannitol, starch or starch hydrolysate, cellulose hydrolysate and molasses; organic acids, such as acetic acid, propionic acid, lactic acid, formic acid, malic acid, citric acid, and fumaric acid; and alcohols, such as glycerol, inositol, mannitol and sorbitol.

Illustrative examples of suitable nitrogen sources include, but are not limited to: ammonia, including ammonia gas and aqueous ammonia; ammonium salts of inorganic or organic acids, such as ammonium chloride, ammonium nitrate, ammonium phosphate, ammonium sulfate and ammonium acetate; urea; nitrate or nitrite salts, and other nitrogen-containing materials, including amino acids as either pure or crude preparations, meat extract, peptone, fish meal, fish hydrolysate, corn steep liquor, casein hydrolysate, soybean cake hydrolysate, yeast extract, dried yeast, ethanol-yeast distillate, soybean flour, cottonseed meal, and the like.

Illustrative examples of suitable inorganic salts include, but are not limited to: salts of potassium, calcium, sodium, magnesium, manganese, iron, cobalt, zinc, copper, molybdenum, tungsten and other trace elements, and phosphoric acid.

Illustrative examples of appropriate trace nutrients, growth factors, and the like include, but are not limited to: coenzyme A, pantothenic acid, pyridoxine-HCl, biotin, thiamine, riboflavin, flavine mononucleotide, flavine adenine dinucleotide, DL-6,8-thioctic acid, folic acid, Vitamin $B_{12}$, other vitamins, amino acids such as cysteine and hydroxyproline, bases such as adenine, uracil, guanine, thymine and cytosine, sodium thiosulfate, p- or r-aminobenzoic acid, niacinamide, nitriloacetate, and the like, either as pure or partially purified chemical compounds or as present in natural materials. Cultivation of the inventive microorganism strain may be accomplished using any of the submerged fermentation techniques known to those skilled in the art, such as airlift, traditional sparged-agitated designs, or in shaking culture.

The culture conditions employed, including temperature, pH, aeration rate, agitation rate, culture duration, and the like, may be determined empirically by one of skill in the art to maximize 2-KLG and/or PQQ production. The selection of specific culture conditions depends upon factors such as the particular inventive microorganism strain employed, medium composition and type, culture technique, and similar considerations. In a particularly preferred embodiment of the present invention, when employing strain NRRL B-3 0035 (ADM291-19), NRRL B-3 0037N (ADM 62A-12A), NRRL B-30036 (ADM 266-13B) or NRRL B-2 1627 (ADM X6L) or a mutant thereof, cultivation takes place at a temperature in the range of 22° C. to 35° C., preferably about 30° C., and at a pH in the range of 6.0 to 8.0, preferably in the range of 6.0 to 7.5, more preferably about 6.5 to 7.5. The culture conditions employed can, of course, be varied by known methods at different timepoints during cultivation, as appropriate, to maximize 2-KLG and/or PQQ production.

After cultivation for a sufficient period of time, such as, for example, from 10 to 150 hours, the 2-KLG and/or PQQ that has accumulated in the cells and/or culture broth is isolated according to any of the known methods including ion exchange chromatography, gel filtration, solvent extraction, affinity chromatography, or any combination thereof. Any method that is suitable with the conditions employed for cultivation may be used; illustrative examples of suitable methods for recovering 2-KLG are described in U.S. Pat. Nos. 5,474,924; 5,312,741; 4,960,695; 4,935,359; 4,877,735; 4,933,289; 4,892,823; 3,043,749; 3,912,592; 3,907,639 and 3,234,105. Illustrative examples of suitable methods for recovering PQQ are described in U.S. Pat. Nos. 4,994,382 and 5,344,768.

According to one such method for the removal of PQQ, solid-liquid separation, such as filtration and/or centrifugation, is applied to the culture broth to effect removal of the cells. Either the supernatant, which is the liquid portion that results after removal of the cells, or culture broth, which contains cells, may be used in further recovery steps. Recovery of PQQ from the supernatant or the culture broth is effected, for example, by ion-exchange chromatography, gel filtration, solvent extraction or affinity chromatography.

Identification of recovered PQQ is made by comparison with pure standard (Fluka Product No. 64682), using, for example, paper chromatography, thin-layer chromatography, gel permeation chromatography, elementary analysis, such as mass spectrometry, nuclear magnetic resonance spectroscopy, absorption spectroscopy or high-performance liquid chromatography (HPLC), or a combination thereof.

Quantitative analysis of PQQ may be made using aD-glucose dehydrogenase activity deletion variant of *Pseudomonas aeruginosa* (Ameyama et al., *FEBS Lett.* 130:179–183 (198 1)) and *E. coli* (Ameyama et al., *Agric. Biol. Chem.* 49:1227–1231 (1985)), UV absorption spectra (Dekker et al., *Eur. J Biochem.* 125:69–73 (1982)), HPLC, gel permeation chromatography combined with mass spectrometry or Fourier transform infrared spectroscopy (FTIR).

According to one such method for recovery of 2-KLG, the microorganisms are first removed from the culture broth by known methods, such as centrifugation or filtration, and the resulting solution concentrated in vacuo. Crystalline 2-KLG is then recovered by filtration and, if desired, purified by recrystallization. Similarly, 2-KLG can be recovered using such known methods as the use of ion-exchange resins, solvent extraction, precipitation, salting out and the like.

When 2-KLG is recovered as a free acid, it can be converted to a salt, as desired, with sodium, potassium, calcium, ammonium or similar cations using conventional methods. Alternatively, when 2-KLG is recovered as a salt, it can be converted to its free form or to a different salt using conventional methods.

In an alternative embodiment of the present invention, an inventive microorganism is cultivated in mixed culture with one or more helper strains. As used herein, "helper strain" is intended to mean a strain of a microorganism that increases the amount of 2-KLG and/or PQQ produced in the inventive process. Suitable helper strains can be determined empirically by one skilled in the art. Illustrative examples of suitable helper strains include, but are not limited to, members of the following genera: Aureobacterium (preferably *A. liquefaciens* or *A. saperdae*), Corynebacterium (preferably *C. ammoniagenes* or *C. glutamicum*), Bacillus, Brevibacterium (preferably *B. linens* or *B. flavum*), Pseudomonas, Proteus, Enterobacter, Citrobacter, Erwinia, Xanthomonas and Flavobacterium. Preferably, the helper strain is *Corynebacterium glutamicum* ATCC 21544.

The helper strain is preferably incubated in an appropriate medium under suitable conditions for a sufficient amount of time until a culture of sufficient population is obtained. This helper strain inoculum may then be introduced into the culture medium for production of 2-KLG and/or PQQ either separately or in combination with the inventive microorganism strain, i.e., a mixed inoculum. Preferably, for production of 2-KLG, the ratio of the amount of the helper strain relative to the amount of strain NRRL B-30035 (ADM 291-19), NRRL B-30037N (ADM 62A-12A) or NRRL B-30036 (ADM 266-13B) is in the range of from 10:1 to 1:10,000. Preferably, for production of PQQ, the ratio of the amount of the helper strain relative to the amount of strain NRRL B-21627 (ADM X6L) is in the range of from 10:1 to 1:10,000.

Another embodiment of the present invention is directed to the novel microorganism strains described above which are useful in fermentation processes for the production of 2-KLG.

An additional embodiment of the invention provides a method of isolating a nontoxic lipopolysaccharide (LPS) from NRRL B-30035 (ADM 291-19), NRRL B-30037N (ADM 62A-12A), NRRL B-30036 (ADM 266-13B) or NRRL B-21627 (ADM X6L) or a mutant thereof. In the context of this embodiment, a mutant is defined as a strain derived from one of the strains of the present invention which produces a nontoxic lipopolysaccharide.

LPS may be purified from the strains of the present invention by any of the known methods described in, for example, Strittmater et al., "Nontoxic Lipopolysaccharide from *Rhodopseudomonas sphaeroides* ATCC 17023, " *J. Bacteriol.* 155:153–158 (1983), Galanos, C. et al., "A new method for extraction of R lipopolysaccharides," *Eur. J Biochem.* 9:245–249 (1969), and Qureshi et al., "Position of Ester Groups in the Lipid A Backbone of Lipopolysaccharides Obtained from *Salmonella typhimurium,*" *J Biol. Chem.* 258:12947–12951 (1983).

One such method for production and purification of LPS from NRRL B-30035 (ADM 291-19), NRRL B-30037N (ADM 62A-12A), NRRL B-30036 (ADM 266-13B) or NRRL B-21627 (ADM X6L) involves culturing in medium comprising 1% Difco Soytone, 1% Difco Yeast Extract, 0.5% Difco Malt Extract, 0.5% NaCl, 0.25% $K_2HPO_4$, 2% mannitol or other suitable carbon source, pH 7.8. Suitable carbon sources can be selected from the group comprising glycerol, mannitol, sorbitol, inositol, glucose and fructose. In the case of ADM 62A-12A, 266-13B, and 291–19 hosts, media without the NaCl is used. Tryptic Soy Broth (Difco) adjusted to pH 7.8 with NaOH could also be used. The cell mass can be grown in liquid media, or in surface culture on media solidified with 1.3% Difco Bacto Agar. The wet bacteria are then washed at least once, with n-butanol containing about 0.1 to 5% acetic acid. The bacteria are then washed further with ethanol, acetone and ether and then dried, for example, in vacuo. The cells are then subjected to phenol-chloroform-petroleum ether extraction and the LPS obtained are optionally treated again with phenol-chloroform-petroleum ether.

The present invention also relates to the strains of the present invention transformed with vectors which optionally include at least one marker gene.

Recombinant constructs may be introduced into the bacterial strains of the present invention using well known techniques such as transduction, transfection, conjugation, and electroporation or other transformation methods. The vector may be, for example, a phage, plasmid, cosmid or a minichromosome.

As defined herein, "host" and "host cells" are synonymous with the cells of the microorganism strains of the present invention.

Polynucleotides of interest may be joined to a vector containing a selectable marker for propagation in the host. A plasmid vector can be introduced in a precipitate, such as a calcium phosphate precipitate, or in a complex with a charged lipid.

Preferred are vectors comprising cis-acting control regions to a polynucleotide of interest. Appropriate trans-acting factors may be supplied by the host, supplied by a complementing vector, or supplied by the vector itself upon introduction into the host.

In certain preferred embodiments in this regard, the vectors provide for specific expression, which may be inducible, mutant-specific and/or condition-specific. Particularly preferred among such vectors are those inducible by environmental factors that are easy to manipulate, such as temperature, nutrient additives or chemical additives. Other suitable environmental factors will be readily apparent to the skilled artisan.

Expression vectors useful in the present invention include chromosomal-, episomal-vectors e.g., vectors derived from plasmids, bacteriophage, and vectors derived from combinations thereof, such as cosmids and phagemids.

A DNA insert of interest should be operatively linked to an appropriate promoter which is preferably a host-derived promoter. The expression constructs will further contain sites for transcription initiation, termination and, in the transcribed region, a ribosome binding site for translation. The coding portion of the mature transcripts expressed by the constructs will include a translation initiating codon appropriate for the host at the beginning and a termination codon appropriately positioned at the end of the polypeptide to be translated.

As indicated, the expression vectors will preferably include at least one marker capable of being selected or screened for. Such markers include amikacin, augmentin (amoxicillin plusclavulonic acid), ampicillin, cefazolin, cefoxitin, ceftazidime, ceftiofur, cephalothin, chloramphenicol, enrofloxacin, erythromycin, florfenicol, gentamicin, imipenem, kanamycin, penicillin, sarafloxicin, spectinomycin, streptomycin, tetracycline, ticarcillin, or tilmicosin resistance genes. Preferred markers include ampicillin, chloramphenicol, erythromycin, kanamycin, penicillin, spectinomycin, streptomycin, and/or tetracycline. Other suitable markers will be readily apparent to the skilled artisan.

A preferred vector is pMF1014-α (M. T. Follettie, "DNA Technology for *Corynebacterium glutamicum:* Isolation and Characterization of Amino Acid Biosynthetic Genes," Ph.D. Dissertation, Massachusetts Institute of Technology, Cambridge, Mass. (1989)), which comprises the pSR1-α replicon and a kanamycin resistance determinant. Specifically, pMF1014-α comprises the pSR1 replicon (Archer, J. A. et al., *J. Gen. Microbiol.* 139:1753–1759 (1993)), and the pSR1-α mutation permitting replicative maintenance of the plasmid in *E. Coli* hosts (Follettie Dissertation, 1989), and the Tn903-derived kanamycin resistance gene from plasmid pUC4K (Taylor, L. A. et al., *Nucleic Acids Res.* 16:358 (1988)). The present invention provides the strains of the present invention, or mutants thereof, comprising pMF1014-α. The present invention provides a biologically pure culture of microorganism strain NRRL B-21627 or a mutant thereof, comprising pMF1014-α.

Introduction of the construct into the host cell can be effected by calcium phosphate transfection, DEAE-dextran mediated transfection, cationic lipid-mediated transfection, electroporation and other transformation methods, transduction, infection or other methods. Such methods are described in many standard laboratory manuals, such as Davis et al., "Basic Methods in Molecular Biology," (1986).

Methods used and described herein are well known in the art and are more particularly described, for example, in J. H. Miller, *Experiments in Molecular Genetics,* Cold Spring Harbor Laboratory Press, Cold Spring Harbor, N.Y. (1972); J. H. Miller, *A Short Course in Bacterial Genetics,* Cold Spring Harbor Laboratory Press, Cold Spring Harbor, N.Y. (1992); M. Singer and P. Berg, *Genes & Genomes,* University Science Books, Mill Valley, Calif. (1991); J. Sambrook, E. F. Fritsch and T. Maniatis, *Molecular Cloning: A Laboratory Manual,* 2d ed., Cold Spring Harbor Laboratory Press, Cold Spring Harbor, N.Y. (1989); P. B. Kaufman et al., *Handbook of Molecular and Cellular Methods in Biology and Medicine,* CRC Press, Boca Raton, Fla. (1995); *Methods in Plant Molecular Biology and Biotechnology,* B. R. Glick and J. E. Thompson, eds., CRC Press, Boca Raton, Fla. (1993); P. F. Smith-Keary, *Molecular Genetics of Escherichia coli,* The Guilford Press, New York, N.Y. (1989); *Plasmids: A Practical Approach,* 2nd Edition, Hardy, K. D., ed., Oxford University Press, New York, N.Y. (1993); *Vectors: Essential Data,* Gacesa, P., and Ramji, D. P., eds., John Wiley & Sons Pub., New York, N.Y. (1994); *Guide to Electroporation and electrofusions,* Chang, D., et al., eds., Academic Press, San Diego, Calif. (1992); *Promiscuous Plasmids of Gram-Negative Bacteria,* Thomas, C. M., ed., Academic Press, London (1989); *The Biology of Plasmids,* Summers, D. K., Blackwell Science, Cambridge, Mass. (1996); *Understanding DNA and Gene Cloning: A Guide for the Curious,* Drlica, K., ed., John Wiley and Sons Pub., New York, N.Y. (1997); *Vectors: A Survey of Molecular Cloning Vectors and Their Uses,* Rodriguez, R. L., et al., eds., Butterworth, Boston, Mass. (1988); *Bacterial Conjugation,* Clewell, D. B., ed., Plenum Press, New York, N.Y. (1993); Del Solar, G., et al., "Replication and control of circular bacterial plasmids," *Microbiol. Mol. Biol. Rev.* 62:434–464 (1998); Meijer, W. J., et al., "Rolling-circle plasmids from *Bacillus subtilis:* complete nucleotide sequences and analyses of genes of pTA1015, pTA1040, pTA1050 and pTA1060, and comparisons with related plasmids from gram-positive bacteria," *FEMS Microbiol. Rev.* 21:337–368 (1998); Khan, S. A., "Rolling-circle replication of bacterial plasmids," *Microbiol. Mol. Biol. Rev.* 61:442–455 (1997); Baker, R. L., "Protein expression using ubiquitin fusion and cleavage," *Curr. Opin. Biotechnol.* 7:541–546 (1996); Makrides, S. C., "Strategies for achieving high-level expression of genes in *Escherichia coli,*" *Microbiol. Rev.* 60:512–538 (1996); Alonso, J. C., et al., "Site-specific recombination in gram-positive theta-replicating plasmids," *FEMS Microbiol. Lett.* 142:1–10 (1996); Miroux, B., et al., "Over-production of protein in *Escherichia coli:* mutant hosts that allow synthesis of some membrane protein and globular protein at high levels," *J. Mol. Biol.* 260:289–298 (1996); Kurland, C. G., and Dong, H., "Bacterial growth inhibited by overproduction of protein," *Mol. Microbiol.* 21:1–4 (1996); Saki, H., and Komano, T., "DNA replication of IncQ broad-host-range plasmids in gram-negative bacteria," *Biosci. Biotechnol. Biochem.* 60:377–382 (1996); Deb, J. K., and Nath, N., "Plasmids of corynebacteria," *FEMS Microbiol. Lett.* 175:11–20 (1999); Smith, G. P., "Filamentous phages as cloning vectors," *Biotechnol.* 10:61–83 (1988); Espinosa, M., et al., "Plasmid rolling cicle replication and its control," *FEMS Microbiol. Lett.* 130:111–120 (1995); Lanka, E., and Wilkins, B. M., "DNA processing reaction in bacterial conjugation," *Ann. Rev. Biochem.* 64:141–169 (1995); Dreiseikelmann, B., "Translocation of DNA across bacterial membranes," *Microbiol. Rev.* 58:293–316 (1994); Nordstrom, K., and Wagner, E. G., "Kinetic aspects of control of plasmid replication by antisense RNA," *Trends Biochem. Sci.* 19:294–300(1994); Frost, L. S., et al., "Analysis of the sequence gene products of the transfer region of the F sex factor," *Microbiol. Rev.* 58:162–210 (1994); Drury, L., "Transformation of bacteria by electroporation," *Methods Mol. Biol.* 58:249–256 (1996); Dower, W. J., "Electroporation of bacteria: a general approach to genetic transformation," *Genet. Eng.* 12:275–295 (1990); Na, S., et al., "The factors affecting transformation efficiency of coryneform bacteria by electroporation," *Chin. J. Biotechnol.* 1:193–198 (1995); Pansegrau, W., "Covalent association of the traI gene product of plasmid RP4 with the 5'-terminal nucleotide at the relaxation nick site," *J. Biol. Chem.* 265:10637–10644 (1990); and Bailey, J. E., "Host-vector interactions in *Escherichia coli*," *Adv. Biochem. Eng. Biotechnol.* 48:29–52 (1993).

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

EXAMPLES

Example 1

Isolation of Strain NRRL B-30035 (ADM 291-19), NRRL B-30037N (ADM 62A-12A), And NRRL B-30036 (ADM 266-13B)

A. Origin, Enrichment and Screening of Soil Samples

Environmental specimens were subjected to microbial enrichment in shake flasks. The resulting mixed cultures were screened to identify those containing at least one microorganism strain capable of producing 2-KLG from L-sorbose. Samples of moist soil, sand, sediment, fruit, berries, humus, and other environmental specimens were collected from various regions of the U.S.A. Each specimen was immediately stored in a cool, ventilated, humidified container. Enrichments were started by adding one gram of soil or specimen to 30 mL of Medium A (Table 1) in a 250 mL baffled shake flask, followed by shaking incubation at 30° C., 230 rpm, for about 2 days.

To screen the enrichments by fermentation, 0.5 to 0.75 mL of each enrichment was transferred to a 250 mL baffled flask containing 30 mL of fresh Medium B (Table 1). These flasks were shaken at 30° C., 230 rpm for about 3 days, after which portions of the mixed culture fermentations were analyzed for 2-KLG content, and cryogenically preserved. For preservation, 2.0 mL of each culture was mixed with 1.0 mL of sterile 40% glycerol in water, then stored at −70° C.

Flasks were screened for 2-KLG production using thin layer chromatography on Whatman LK5 Silica Gel 150 plates, 250 mm thickness (Catalog No. 4855-820). The plates were spotted with 5 $\mu$L of centrifuged culture broth, and developed for 5–6 hours in solvent (157 mL of n-propanol; 39 mL of deionized water; 4 mL of 1% phosphoric acid; 0.4 mL of glacial acetic acid). The plates were air dried and then sprayed with 0.125 g of tetrazolium blue chloride dissolved in 25 mL of methanol and 25 mL of 6N sodium hydroxide, after which they were baked at 60° C. for 5 minutes. Sorbose and 2-KLG were visualized as purple spots on the finished plates, and were identified by comparison with a standard containing 10 g/L each of 2-KLG and L-sorbose.

Production of 2-KLG was quantitated by HPLC. Samples were prepared by 1:10 dilution in mobile phase, followed by filtration through 0.45 $\mu$m porous membranes. Mobile phase contained 1.1 mL of ACS grade sulfuric acid diluted to 4.0 L using Milli-Q water. Samples of 100 $\mu$L each were loaded on two 2 mm×300 mm×7.8 mm Aminex HPX-87H columns (BioRad) arranged in series to provide a total column length of 600 mm, preceded by a guard column of the same resin. The column was run at 55° C. using a flow rate of 0.6 mL/min. L-sorbose and 2-KLG were detected using a Waters Model No. 410 differential refractometer, and were identified by comparison to a standard containing 2-KLG and L-sorbose.

Thirty-three (33) of the mixed culture fermentations produced 2-KLG, in amounts ranging from 1.8 to 9.3 g/L. The mixed culture fermentations from which strains NRRL B-30035 (ADM 291-19), NRRL B-30037N (ADM 62A-12A), and NRRL B-30036 (ADM 266-13B) were later isolated (Example 1B) produced 6.9 g/L, 9.3 g/L, and 5.4 g/L of 2-KLG, respectively.

B. Isolation and Testing of Monocultures

Pure cultures of microorganisms capable of producing 2-KLG from L-sorbose, either in monoculture or in mixed culture with other microorganisms, were isolated from the enrichments described above. Eleven mixed-culture enrichments from Example 1A were chosen on the basis of their superior 2-KLG production. These were thawed and diluted in 10-fold serial increments using Medium A, after which 0.1 mL of each dilution was spread on the surface of a Medium A agar plate. The plates were incubated at 30° C. for 24 hours, then examined under 8- to 40-fold magnification. Attention to the smallest, slowest-growing colonies was necessary in order to recover 2-KLG producing strains from the dilution plates. Several examples of each colony type and size were selected and subcultured on fresh Medium A plates, after which the dilution plates were returned to 30° C. for 24 hours. Additional slow-growing colonies were selected from the dilution plates and subcultured after the second incubation period. Each strain was streak-purified for 1–3 cycles on either Medium A plates or on PYM plates (10 g/L peptone; 10 g/L yeast extract; 0.5 g/L glycerol; 30 g/L mannitol; 20 g/L agar). The pure strains were cryogenically preserved at −70° C. in PYM liquid medium containing 20% glycerol. A total of 118 pure strains were recovered from the eleven enrichment mixtures.

The 118 new strains were tested for their potential to convert L-sorbose into 2-KLG in shake flasks. To account for the possibility that 2-KLG production might require the combined activity of two or more microorganisms, each new isolate was tested in pairwise combination with all other strains originating from the same enrichment, as well as in pure culture. To prepare inoculum, each strain was cultured on PYM agar for 24 hours, after which a large loop of cells was suspended in sterile buffer containing 50 mM sodium phosphate, 0.4% sodium chloride, and 0.05% mannitol, pH 7.2. For each pure-strain or paired-strain test, a 250 mL baffled flask containing thirty mL of Medium C (Table 1) was inoculated with 0.2 mL of cell suspension of each of the relevant strains. These flasks were shaken at 30° C., 230 rpm for 24 hours, after which 1.0 mL was transferred to 30 mL of fermentation Medium D (Table 1). The fermentation flasks were shaken at 30° C., 230 rpm for three days, then the broth was analyzed for 2-KLG and sorbose content using TLC and HPLC. Flasks containing strains NRRL B-30035 (ADM 291-19), NRRL B-30037N (ADM 62A-12A), and NRRL B-30036 (ADM 266-13B) showed an overall pattern of higher 2-KLG levels than flasks not containing these strains. These strains were singled out for further studies as 2-KLG producing candidates.

TABLE 1

Media employed in Example 1

| Ingredient (g/L) | A | B | C | D |
|---|---|---|---|---|
| L-sorbose | 20.0 | 50.0 | 20.0 | 50.0 |
| D-glucose | 2.0 | 0.0 | 1.0 | 0.0 |
| Corn Steep Liquor dry solids | 10.0 | 10.0 | 15.0 | 15.0 |
| $FeSO_4.7H_2O$ | 0.1 | 0.1 | 0.1 | 0.1 |
| Yeast Nitrogen Base | 1.7 | 1.7 | 1.7 | 1.7 |
| $CaCO_3$ | 6.0 | 20.0 | 6.0 | 20.0 |
| Cycloheximide | 0.005 | 0.005 | 0.0 | 0.0 |

* The glucose, corn steep liquor, iron sulfate and calcium carbonate were adjusted to pH 7.9, then autoclaved for 20 minutes. The remaining ingredients were adjusted to pH 6.3, then sterilized by filtration. The finished medium had a pH in the range of 7.1–7.4. Yeast Nitrogen Base was Difco product #0335-15-9.

Example 2

Production of 2-KLG from L-SORBOSE by Strains NRRL B-30035 (ADM 291-19), NRRL B-30037N (ADM 62A-12A), and NRRL B-30036 (ADM 266-13B) in Shake Flasks For each tested strain, one loop of fresh culture grown on agar medium was inoculated into a 250 mL baffled shake flask containing 20 mL of seed Medium A or B (Table 2), which was shaken at 30° C. for 22–24 hours at 240 rpm. Two mL of seed contents were used to inoculate 25 mL of fermentation Medium C or D (Table 2) in a 250 mL baffled shake flask, and the flasks were shaken for 72–92 hours at 30° C., 240 rpm. The broth was subsequently withdrawn and analyzed by HPLC. The 2-KLG production results are shown in Table 3.

TABLE 2

Media employed in Examples 2 and 3

| Ingredient(amount/L) | a | b | c | d |
|---|---|---|---|---|
| N-Z Soy ™ (Sheffield) | 0 | 10 g | 0 | 0 |
| Soy Soluble* | 0 | 0 | 0 | 6.0 g |
| Corn Steep Liquor (dry solids) | 20.0 g | 20.0 g | 20.0 g | 20.0 g |
| Bactopeptone (Difco) | 10.0 g | 0 | 15.0 g | 0 |
| L-sorbose | 0 | 0 | 100.0 g | 125.0 g |

TABLE 2-continued

Media employed in Examples 2 and 3

| Ingredient(amount/L) | a | b | c | d |
|---|---|---|---|---|
| D-sorbitol | 10.0 g | 10.0 g | 0 | 0 |
| D-mannitol | 10.0 g | 20.0 g | 15.0 g | 0 |
| Niacinamide | 0 | 0.05 g | 0.05 g | 0 |
| Thiamine | 0 | 0.3 g | 0.3 g | 0 |
| Pantothenic acid | 0 | 0.4 g | 0.4 g | 0 |
| p-aminobenzoic acid | 0 | 0.2 g | 0.2 g | 0 |
| $MgSO_4.7H2O$ | 0 | 0 | 2.5 g | 0 |
| $CaCO_3$ | 40.0 g | 0 | 25.0 g | 50.0 g |
| pH (before autoclave) | 6.5 | 6.7 | 7.2 | 7.2 |

*Soy soluble was a liquid waste fraction from soy processing. The amount is expressed as grams of dried solids per liter of medium.

TABLE 3

2-KLG production from L-sorbose by pure cultures in shaker flasks

| Strain | Seed Medium | Production Medium | 2-KLG, g/L | Yield %* |
|---|---|---|---|---|
| 62A-12A | a (24 hr) | c (92 hr) | 10.5 | 82.0 |
| 62A-12A | b (22 hr) | d (72 hr) | 3.8 | 64.4 |
| 266-13B | a (24 hr) | c (92 hr) | 7.1 | 69.2 |
| 266-13B | b (22 hr) | d (72 hr) | 4.2 | 76.4 |
| 291-19 | a (24 hr) | c (92 hr) | 5.8 | 59.8 |
| 291-19 | b (22 hr) | d (72 hr) | 3.9 | 46.4 |

*Yield is expressed as grams of 2-KLG produced per 100 grams of initial L-sorbose in the reaction.

Example 3

Production of 2-KLG from L-SORBOSE by Mixed Cultures Comprised of Producer Strains NRRL B-30035 (ADM 291-19), or NRRL B-30037N (ADM 62A-12A), or NRRL B-30036 (ADM 266-13B), in Co-culture with a Second Organism For each producer strain, one loop of fresh culture grown on agar medium was inoculated into a 250 mL baffled shake flask containing 20 mL of Medium A (Table 2), followed immediately by inoculation with 100 uL of a frozen culture of *Aureobacterium liquefaciens* strain X6S. The flasks were shaken at 240 rpm for 22–24 hours at 30° C. Two mL of this culture was transferred to a 250 mL baffled shake flask containing 25 mL of Medium C, which was then shaken for 72–92 hours at 30° C., 240 rpm. The broth was subsequently withdrawn and analyzed by HPLC. The 2-KLG production results are shown in Table 4.

TABLE 4

Production of 2-KLG from L-sorbose by mixed cultures in flasks

| Producer | Helper | Seed Medium | Production Medum | 2-KLG, g/L | Yield %* |
|---|---|---|---|---|---|
| 62A-12A | X6S | a (24 hr) | c (92 hr) | 46.8 | 74.5 |
| 266-13B | X6S | a (24 hr) | c (92 hr) | 34.2 | 68.1 |
| 291-19 | X6S | a (24 hr) | c (92 hr) | 32.1 | 59.4 |

*Yield is expressed as grams of 2-KLG produced per 100 grams of initial L-sorbose in the reaction.

Example 4

Production of PQQ by Strains NRRL B-30035 (ADM 291-19), NRRL B-30037N (ADM 62A-12A), NRRL B-30036 (ADM 266-13B), and NRRL B-21627 (ADM X6L) in Shake Flasks Strain NRRL B-30035 (ADM 291-19), NRRL B-30037N (ADM 62A-12A), NRRL B-30036 (ADM 266-13B), or NRRL B-21627 (ADM X6L), is inoculated into 10 ml of DM Basal Medium (Table 5), pH 7.8 and shaken at 300 rpm, 30° C., until a maximum optical density at 600 nm wavelength is reached. In the case of ADM 62A-12A, 266-13B, and 291-19 medium without the NaCl is used. Five ml of this culture was transferred to 500 ml of fresh Medium in a 2 L baffled flask, which was incubated with shaking at 300 rpm, 30° C., for a time sufficient to reach a maximum optical density at 600 nm wavelength.

To determine the amount of PQQ in the medium, a sample is removed at a predetermined time and centrifuged to obtain a supernatant. The supernatant is analyzed according to the methods of U.S. Pat. Nos. 4,994,382 and/or 5,344,768 or by gel permeation chromatography coupled with mass spectrometry.

Example 5

Extraction of a Nontoxic Lipopolysaccharide from Strains NRRL B-30035 (ADM291-19), NRRL B-30037N (ADM 62A-12A), NRRL B-30036 (ADM 266-13B), and NRRL B-21627 (ADM X6L)

NRRL B-30035 (ADM291-19), NRRL B-30037N (ADM 62A-12A), NRRL B-30036 (ADM 266-13B), or NRRL B-21627 (ADM X6L) is cultured in medium comprising 1% Difco Soytone, 1% Difco Yeast Extract, 0.5% Difco Malt Extract, 0.5% NaCl, 0.25% $K_2HPO_4$, 2% mannitol, 2% myo-inositol, or 2% glucose, or other suitable carbon source, pH 7.8 and shaken at 300 rpm, 30° C. In the case of NRRL B-30035 (ADM 291-19), NRRL B-30037N (ADM 62A-12A), NRRL B-30036 (ADM 266-13B), media without NaCl is used. The cells are then harvested and then washed three times with water. 120 g of the wet bacteria are then washed three times, each time with 600 ml of n-butanol containing about 1% acetic acid. The bacteria are then washed further with ethanol, acetone and ether (for each, three times with 600 ml) and dried in vacuo.

The dried bacteria are placed in a centrifuge vessel and the extraction mixture (200 ml) is added. The extraction mixture contains liquid phenol (90 g dry phenol +11 ml water), chloroform and petroleum ether (b. p. 40–60°) in a volume ratio of 2:5:8, respectively. This mixture is monophasic when the phenol used is dry. If water is present in the original phenol preparation, the mixture is cloudy and can be made clear by adding solid phenol. The suspension is then homogenized for 2 min with cooling so that the temperature remains between 5° and 20° C. This treatment is not meant to break the bacteria but to obtain them in a fine suspension. If the bacteria are already finely suspended, stirring the mixture for a few minutes is sufficient. Sometimes the suspension is very viscous after homogenization. In this case, more extraction mixture is added. The bacteria are then centrifuged off (5000 rev./min, 15 min) and the supernatant which contained the lipopolysaccharide is filtered through filter paper into a round flask. The bacterial residue is extracted once more with the same amount of extraction mixture, stirred and centrifuged as above and the supernatant is added to the first extract. The extraction could be repeated for a third time.

The pooled supernatant solutions have a light yellow to dark brown color. Petroleum ether and chloroform are then removed completely on a rotary evaporator at 30–40° (or in high vacuum at below 0°). Should the remaining phenol now crystallize, sufficient water is added to dissolve it. The solution is transferred into a glass centrifuge pot and water added dropwise until the lipopolysaccharide precipitates. Addition of water is stopped when the lipopolysaccharide starts settling down after the mixture is allowed to stand for 1 to 2 min. Although precipitation of the lipopolysaccharide is complete long before the phenol is saturated with water, care must be taken not to add too much water as this causes formation of two phases. The precipitated lipopolysaccharide is then centrifuged (3000 rev./min, 10 min), the supernatant is decanted, and the tube is allowed to stand for 2 to 3 min upside down. It is then wiped inside with filter paper. The precipitate is washed two to three times with small portions of 80% phenol (about 5 ml) and the inside of the tube is wiped with filter paper after decantation of the supernatant. Finally, the precipitate is washed three times with ether to remove any remaining phenol, and dried in vacuo. The lipopolysaccharide is taken up in distilled water (50 ml), warmed to 45° C., and vacuum is carefully applied to remove the air. It is then shaken for a few minutes whereby a viscous, sometimes very viscous, solution is obtained. The viscosity may be reduced by placing the solution in an ultra vibrator for 5 min. The lipopolysaccharide solution is centrifuged at high speed (100,000×g, 4 h). The resulting sediment is clear and transparent, so that it is sometimes difficult to recognize until the supernatant is decanted. The lipopolysaccharide is redissolved in water and freeze-dried.

TABLE 5

Defined basal medium (DM) for isolate characterization

| Ingredient | amount |
| --- | --- |
| yeast extract | 0.5 g/l |
| mannitol | 10 g/l |
| 21 amino acids (includes hydroxyproline) | 100 mg/l each |
| bases: adenine, uracil, guanine, thymine, cytosine | 100 mg/l each |
| Mineral salts: | |
| $MgCl_2.6H_2O$ | 1 g/l |
| $NaSO_4$ | 1 g/l |
| NaCl | 5 g/l |
| KCl | 350 mg/l |
| $K_2HPO_4$ | 140 mg/l |
| $CaCl_2.2H_2O$ | 75 mg/l |
| NaBr | 50 mg/l |
| $H_3BO_3$ | 20 mg/l |
| $Na_2WO_4.2H_2O$ | 3 mg/l |
| Trace element solution | 1X |
| Vitamin solution | 1X |
| 250 mM MOPS; pH 7.2 | |
| Filter sterilize | |
| 100X Trace element solution: | |
| Nitrilotriacetate | 150.0 mg/l |
| $FeSO_4.7H_2O$ | 140.0 mg/l |
| $MnSO_4.H_2O$ | 30.5 mg/l |
| $CoCl_2.6H_2O$ | 30.5 mg/l |
| $NiCl_2.6H_2O$ | 20.0 mg/l |
| $Na_2MoO_4.2H_2O$ | 0.1 mg/l |
| $CuSO_4.5H_2O$ | 0.1 mg/l |
| 100X Vitamin solution: | |
| Pyridoxine-HCl | 10.0 mg/l |
| r-Aminobenzoic acid | 5.0 mg/l |
| Nicotinic acid | 5.0 mg/l |
| DL-Calcium pantothenate | 5.0 mg/l |
| Thiamine-HCl | 5.0 mg/l |
| DL-6,8-Thioctic acid | 5.0 mg/l |
| Riboflavin | 4.0 mg/l |
| Biotin | 2.0 mg/l |
| Folic acid | 2.0 mg/l |
| Vitamin $B_{12}$ | 0.1 mg/l |

Example 6

Strain Transformation with a Vector

Bacterial host strain ADM X6L was transformed by electroporation with the plasmid vector pMF1014-α, which comprises the pSR1-a replicon and a kanamycin resistance determinant. The pMF1014-α plasmid was then re-isolated from the resulting ADM X6L transformant and subsequently used to transform an *E. coli* host. The example demonstrates transformation of the ADM strains with a vector, selection of transformants by expression of kanamycin resistance in the ADM host, maintenance of the plasmid as an extrachromosomal element in the ADM host, and the use of pMF1014-α as a new *E. coli* ADM host strain shuttle vector.

Plasmid pMF1014-α (M. T. Follettie, "DNA Technology for *Corynebacterium glutamicum*: isolation and characterization of amino acid biosynthetic genes," Ph.D. Dissertation, MIT, U.S.A., 1989) DNA was isolated using the materials and procedures provided in the "Wizard Plus Midipreps" DNA Purification System (Promega), from a 50 ml overnight culture of *E. coli* DH5αMCR/pMF1014-α cultured on Luria broth (1% Difco Tryptone, 0.5% Difco Yeast Extract, 0.5% NaCl) with 50 μg/ml of kanamycin sulfate.

To prepare competent ADM X6L host cells, a single colony of ADM X6L was inoculated into 10 ml of X6L Medium (1% Difco Soytone, 1% Difco Yeast Extract, 0.5% Difco Malt Extract, 0.5% NaCl, 0.25% K2HPO4, 2% mannitol, pH 7.8) and shaken at 300 rpm, 30° C., until an $OD_{600}$ of 0.8 absorption units was reached. In the case of ADM 62A-12A, 266-13B, and 291-19 hosts, X6L Medium without the NaCl is used. Five ml of this culture was transferred to 500 ml of fresh X6L medium in a 2 L baffled flask, which was incubated with shaking at 300 rpm, 30° C., for a time sufficient to reach an $OD_{600}$ of 1.0 absorption units. The mature culture was chilled quickly, and a temperature of 2–4° C. was maintained during the subsequent steps. The cells were harvested by centrifugation and washed by two cycles of resuspension in 500 ml of ice-cold water followed by recentrifugation. The pellet from the second wash was suspended in 40 ml of ice-cold 10% glycerol, mixed, and recentrifuged. The volume of this pellet was estimated, and the pellet was suspended in an equivalent volume of ice cold 10% glycerol. The resulting transformation-competent cell suspension was aliquoted into microcentrifuge tubes, 40 μL per tube, and stored at −80° C.

Two μL of a cold solution containing 140 μg/ml of purified pMF104-α DNA in water was added to 40 μL of cold, competent ADM X6L cells, and mixed. The cell-DNA mixture was transferred to a pre-chilled electroporation cuvette (1 mm cuvette, Catalog No. 940-00-100-5, Eppendorf Scientific, Inc.), quickly transferred to a "BioRad Gene Pulser II" electroporation device and pulsed at 1.5 kV, 25 μF, 200 ohms. Immediately after the pulse, 1 ml of room temperature X6L Medium was added to the pulsed cells, and the mixture was transferred to a 10-ml sterile test tube and incubated with shaking at 300 rpm, 30° C. After two hours of incubation to allow expression of kanamycin resistance, 1.04 ml of the cell suspension was removed and microcentrifuged for 2 minutes at 14,000 rpm. 0.9 ml of the supernatant was removed, the cell pellet was suspended in the remaining supernatant, and the cell suspension was spread on a petri plate of X6L Medium containing 20 μg/ml kanamycin and 1.3% Difco Bacto Agar. The plate was incubated for 2 days at 30° C. Twenty kanamycin-resistant ADM X6L transformant colonies were obtained by this procedure.

The X6L transformants maintained the pMF1014-α plasmid as an extrachromosomal element. To demonstrate this, plasmid DNA was reisolated from the X6L transformants using the procedure outlined above for *E. coli*, except that the transformed X6L cells were grown in X6L Medium containing 40 μg/ml kanamycin. The plasmid DNA isolated from the X6L transformants had the same size as the original pMF1014-α a plasmid, as demonstrated by agarose gel electrophoresis. The plasmid isolated from the X6L transformant still carried the kanamycin resistance gene and *E. coli* replication determinants. To demonstrate this, competent *E. coli* cells were prepared by the method of Letterberg and Cohen (J. Bact. 119:1072–1074, 1964), and transformed with plasmid DNA from the X6L transformants using the method of D. A. Morrison (J. Bact. 132:349–351, 1977). *E. coli* cells transformed by this method acquired kanamycin resistance, and showed the presence of a plasmid having the same size as the original plasmid pMF1014-α.

What is claimed is:

1. A monoculture of a bacterial strain comprising:

(a) a strain selected from the group consisting of NRRL B-30035 (ADM 291-19), NRRL B-30037N (ADM 62A-12A), and NRRL B-30036 (ADM 266-13B); or (b) a mutant derived from any strain listed in (a).

2. A method for the production of 2-keto-L-gulonic acid, comprising culturing the strain according to claim 1 in a medium comprising L-sorbose for a time sufficient for said L-sorbose to be converted to 2-keto-L-gulonic acid; and recovering said 2-keto-L-gulonic acid.

3. The method according to claim 2, further comprising converting said 2-keto-L-gulonic acid to ascorbic acid or a salt thereof.

4. The method according to claim 2, wherein said culturing is performed at a pH of about 6.0 to 8.0.

5. The method according to claim 2, wherein said culturing is performed at a temperature of about 22° C. to about 35° C.

6. The monoculture of claim 1 comprising bacterial strain NRRL B-30035 (ADM 291-19) or a mutant derived from said strain.

7. The monoculture of claim 6, comprising bacterial strain NRRL B-30035 (ADM 291-19).

8. The monoculture of claim 1 comprising bacterial strain NRRL B-30037N (ADM 62A-12A) or a mutant derived from said strain.

9. The monoculture of claim 8, comprising bacterial strain NRRL B-30037N (ADM 62A-12A).

10. The monoculture of claim 1 comprising bacterial strain NRRL B-30036 (ADM 266-13B) or a mutant derived from said strain.

11. The monoculture of claim 10, comprising bacterial strain NRRL B-30036 (ADM 266-13B).

12. A cell culture comprising:

(a) a bacterial strain selected from the monoculture of claim 1; and (b) a synthetic cell culture medium.

13. The cell culture of claim 12 comprising bacterial strain NRRL B-30035 (ADM 291-19) or a mutant derived from said strain.

14. The cell culture of claim 12 comprising bacterial strain NRRL B-30037N (ADM 62A-12A) or a mutant derived from said strain.

15. The cell culture of claim 12 comprising bacterial strain NRRL B-30036 (ADM 266-13B) or a mutant derived from said strain.

16. The cell culture of claim 12 further comprising L-sorbose.

17. A method for the production of 2-keto-L-gulonic acid, comprising culturing the cell culture of claim 16 for a time sufficient for said L-sorbose to be converted to 2-keto-L-gulonic acid.

18. The method of claim 17, further comprising converting said 2-keto-L-gulonic acid to ascorbic acid or a salt thereof.

19. The method of claim 17, wherein said culturing is performed at a pH of 6.0 to 8.0.

20. The method according to claim 17, wherein said culturing is performed at a temperature of 22° C. to 35° C.

\* \* \* \* \*